(12) United States Patent
Okamoto (10) Patent No.: US 10,105,038 B2
(45) Date of Patent: Oct. 23, 2018

(54) INSERTION APPARATUS (71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/479,406

(22) Filed: Apr. 5, 2017

(65) Prior Publication Data
US 2017/0202440 A1 Jul. 20, 2017

Related U.S. Application Data (63) Continuation of application No. PCT/JP2015/074725, filed on Aug. 31, 2015.

(30) Foreign Application Priority Data

Mar. 30, 2015 (JP) .................. 2015-069834

(51) Int. Cl.
A61B 1/00 (2006.01)
A61B 1/01 (2006.01)
(Continued)

(52) U.S. Cl.
CPC .............. *A61B 1/01* (2013.01); *A61B 1/0008* (2013.01); *A61B 1/0016* (2013.01);
(Continued)

(58) Field of Classification Search
CPC ..... A61B 1/01; A61B 1/00154; A61B 1/0016; A61B 1/0008; A61B 1/0057; G02B 23/2476
See application file for complete search history.

(56) References Cited

U.S. PATENT DOCUMENTS

2011/0065994 A1  3/2011 Kudoh et al.
2012/0004504 A1* 1/2012 Frassica ............ A61M 25/0017
                                                        600/115
(Continued)

FOREIGN PATENT DOCUMENTS

EP    1 454 588 A2    9/2004
EP    2229868 A1     9/2010
(Continued)

OTHER PUBLICATIONS

International Search Report dated Nov. 24, 2015 issued in PCT/JP2015/074725.
(Continued)

*Primary Examiner* — Timothy J Neal
(74) *Attorney, Agent, or Firm* — Scully, Scott, Murphy & Presser, P.C.

(57) ABSTRACT

An insertion apparatus includes: a flexible tube; an electric driving source arranged on a proximal end side of the flexible tube; a driven portion arranged on a distal end of the flexible tube; and a single driving force transmitting member inserted in the flexible tube and formed by being wound in a coil shape. For the driving force transmitting member, first torsional rigidity in a first rotating state of being rotated in a direction of being wound in the coil shape is set higher than second torsional rigidity in a second rotating state of being rotated in an opposite direction; and the driven portion performs a first motion by the first rotating state and performs a second motion requiring a larger amount of force than the first motion by the second rotating state.

4 Claims, 5 Drawing Sheets (51) Int. Cl.
*A61B 1/005* (2006.01)
*G02B 23/24* (2006.01)
(52) U.S. Cl.
CPC ........ *A61B 1/0057* (2013.01); *A61B 1/00135* (2013.01); *A61B 1/00154* (2013.01); *G02B 23/2476* (2013.01); *A61B 1/00156* (2013.01)

(56) References Cited

U.S. PATENT DOCUMENTS

2013/0137927 A1   5/2013  Nakamura et al.
2013/0310646 A1*  11/2013 Dejima .............. A61B 1/00154
                                                  600/114
2014/0298932 A1   10/2014 Okamoto

FOREIGN PATENT DOCUMENTS

JP      2010-213969 A    9/2010
JP      2013-111341 A    6/2013
WO   WO 2014/084135 A1   6/2014

OTHER PUBLICATIONS

Japanese Office Action dated Sep. 27, 2016 issued in JP 2016-536261.
Extended Supplementary European Search Report dated Jun. 13, 2018 in European Patent Application No. 15 88 7709.2.

* cited by examiner

ENLARGED VIEW OF PORTION A

INSERTION APPARATUS

CROSS REFERENCE TO RELATED APPLICATION

This application is a continuation application of PCT/JP2015/074725 filed on Aug. 31, 2015 and claims benefit of Japanese Application No. 2015-069834 filed in Japan on Mar. 30, 2015, the entire contents of which are incorporated herein by this reference.

BACKGROUND OF THE INVENTION

1. Field of the Invention

The present invention relates to an insertion apparatus having a flexible tube portion on a proximal end side of an insertion portion to be inserted into an examined part.

2. Description of the Related Art

An endoscope is one of insertion apparatuses and is used in a medical field, an industrial field and the like. The endoscope has an elongated insertion portion to be inserted into an examined part. The insertion portion is provided with a flexible tube having flexibility.

An endoscope used in the medical field makes it possible to perform observation of an organ and the like by inserting the insertion portion into a body. In addition, in a configuration in which the endoscope is provided with a treatment instrument insertion channel, it is possible to perform various kinds of treatments and the like by introducing a treatment instrument into a body via the channel.

In comparison, an endoscope used in the industrial field makes it possible to perform observation and inspection about presence or absence of a crack, presence or absence of corrosion and the like by inserting the elongated insertion portion into a jet engine, piping in a factory and the like.

Some endoscopes are provided with a bending portion on a distal end side of the flexible tube constituting the insertion portion. In the endoscopes provided with the bending portion, it is possible to change an orientation of the distal end portion of the insertion portion by bending the bending portion in a desired direction.

The bending portion performs a bending motion, for example, by an operator performing an operation of rotating a knob for up/down or a knob for left/right provided on the operation portion to directly pull or loosen a bending wire.

A maximum bending angle of the bending portion of an endoscope in one direction and a maximum bending angle in the other direction, which is a direction opposite to the one direction, may be different in some cases. For example, in a case of an endoscope configured such that a maximum bending angle in an upward direction is 210 degrees, and a maximum bending angle in a downward direction is 120 degrees, the burden applied on hand fingers further increases at time of causing the bending portion to bend at an angle of more than 120 degrees.

Therefore, in order to reduce the burden applied on the hand fingers, an endoscope having an electric bending mechanism portion configured to pull a bending wire using an electric mechanism to resolve the burden applied on the operator's hand fingers is proposed.

Note that, as an electric operation function portion of an endoscope for reducing the burden on an operator, electric mechanism portions such as an insertion assisting tool and a power assist mechanism portion are well-known in addition to the electric bending mechanism portion described above.

The insertion portion assisting mechanism portion has a spiral shape portion, and the spiral shape portion is rotatably disposed at a predetermined position on an outer circumferential surface of the insertion portion which is on a more proximal end side of the endoscope than the bending portion. The spiral shape portion of the insertion portion assisting mechanism portion is configured to be rotated in a spiral winding direction or in a direction opposite to the spiral winding direction around an axis of the insertion portion by driving force of a motor.

In a state in which the spiral shape portion is being rotated in the spiral winding direction, propulsion that causes the insertion portion to move forward is given to the insertion portion, the propulsion being caused by screw action caused by an outer surface of the spiral shape portion coming into contact with a body cavity wall. On the other hand, in a state in which the spiral shape portion of the insertion portion assisting mechanism portion is being rotated in the direction opposite to the spiral winding direction, propulsion that causes the insertion portion to move backward is given to the insertion portion, the propulsion being caused by screw action.

As a result, at time of performing a hand-side operation for causing the insertion portion to move forward or a hand-side operation for causing the insertion portion to move backward, the operator can obtain the propulsion that causes the insertion portion to move forward or the propulsion that causes the insertion portion to move backward, and the burden on the operator is reduced.

The power assist mechanism portion is provided with a plurality of C-shaped rings around which respective bending wires are wound, one pulley on which each of the C-shaped rings is freely disposed, and a motor configured to cause the pulley to rotate. The pulley is continuously rotated by driving force of the motor, and is configured so that, when a bending operation is performed, rotation force of the pulley is transmitted to the bending wires via the C-shaped rings.

By the rotation force of the pulley being transmitted to the bending wires via the C-shaped rings, an amount of pulling operation force is reduced in comparison with a case of directly pulling the bending wires. Thereby, it becomes possible to perform a smooth bending operation, and the burden on the operator is reduced.

International Publication No. 2014/084135 discloses an endoscope apparatus configured to transmit driving force of an electric motor, which is a driving portion, to an electric operation function portion such as an insertion portion assisting mechanism portion by a flexible driving shaft to reduce the burden on an operator.

In the endoscope apparatus, a winding direction for which torsional rigidity of the driving shaft is set high is caused to correspond to a rotation direction of the driving shaft. Therefore, in a state in which the driving shaft is being rotated in the winding direction, force that shrinks the driving shaft, in other words, force that shortens the driving shaft acts on the driving shaft. Then, the torsional rigidity of the driving shaft becomes high by the force that shortens the driving shaft acting on the shaft, and it becomes possible to certainly transmit rotational driving force.

Note that the driving shaft is configured such that one of both ends is a fixed end which is fixed, and the other end is a free end which freely moves forward and backward relative to an axial direction.

The electric bending mechanism portion of International Publication No. 2014/084135 described above is configured such that a maximum bending angle in a bending direction on one side of a bending portion and a maximum bending angle in a bending direction on the other side, which is an opposite direction, are different. Therefore, an amount of force that pulls one bending wire corresponding to the bending direction in which the maximum bending angle is large becomes larger in comparison with an amount of force that pulls the other bending wire. Therefore, the winding direction of the driving shaft and the rotation direction of the driving shaft are caused to correspond to each other, and the rotation direction of the driving shaft is caused to correspond to a rotation direction in which an amount of pulling force of a pulley is larger.

As a result, at time of causing a bending portion to bend in the bending direction in which the maximum bending angle is larger, driving force of the driving portion is efficiently and certainly transmitted by the driving shaft to cope with increase in the amount of pulling force.

On the other hand, as for the insertion assisting tool, when an insertion portion is introduced into a digestive tract of a digestive organ, resistance between an outer circumferential surface of the insertion portion and a body wall gradually increases accompanying increase in an insertion length. Therefore, larger propulsion is required at the time of inserting the insertion portion in comparison with a case of pulling out the insertion portion. Therefore, the winding direction of the driving shaft is caused to correspond to the rotation direction of the driving shaft.

Figure 1A:
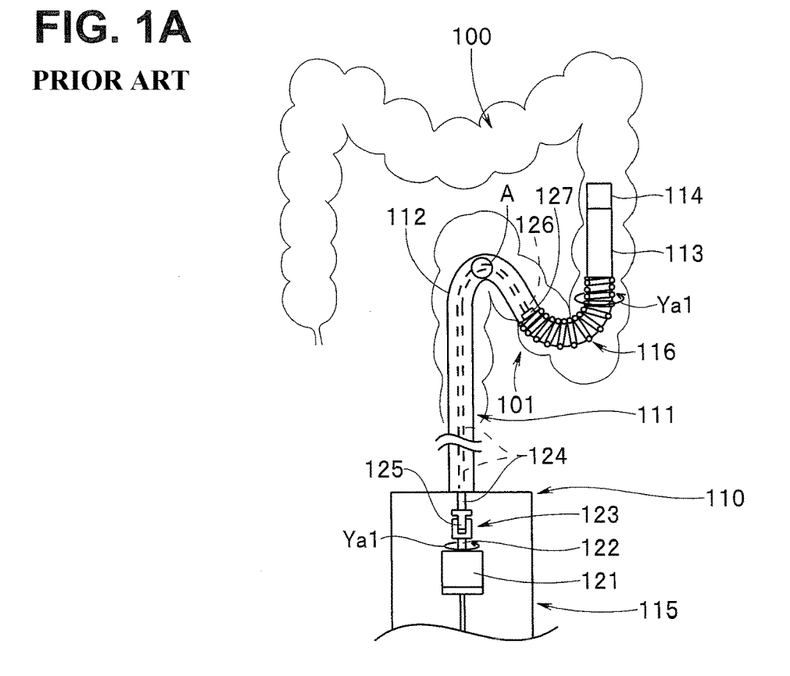
FIG. 1A is a diagram illustrating a configuration and action of an insertion portion assisting mechanism portion that an endoscope has.

More specifically, at time of inserting an insertion portion 111 of an endoscope 110 toward a depth of a large intestine 100 while obtaining propulsion, as shown in FIG. 1A, for example, a driving axle 122 of a motor 121 provided in an operation portion 115 is caused to rotate in a direction Ya1, and the rotational driving force is transmitted to a driving shaft 124 via a coupling portion 123, and the driving shaft 124 is rotated in the direction Ya1 similarly to the driving axle 122.

As a result, rotational driving force of the motor 121 is efficiently transmitted by the driving shaft 124, and a spiral shape portion 116 which is rotatable on an outer circumferential side of a flexible tube 112 is rotated in the direction Ya1, which is a clockwise direction, so that propulsion for causing the insertion portion 111 to move forward is given from the spiral shape portion 116.

Note that reference numeral 113 denotes a bending portion, and reference numeral 114 denotes a distal end rigid portion.

Figure 1B:
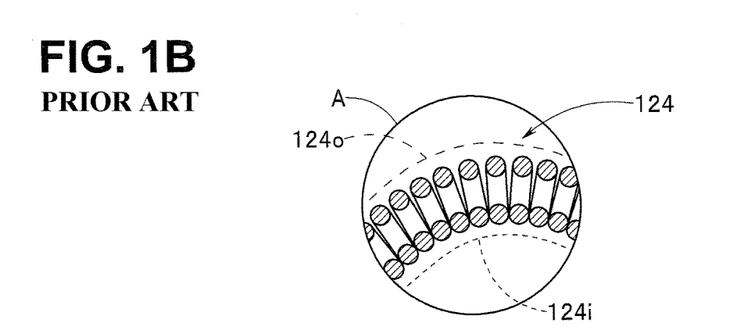
FIG. 1B is a diagram illustrating the configuration and action of the insertion portion assisting mechanism portion that the endoscope has.

In an endoscope apparatus disclosed in International Publication No. 2014/084135, when the driving shaft 124 disposed in the flexible tube 112 passes, for example, through a bent portion of a sigmoid colon 101 or the like in a state in which the insertion portion 111 of the endoscope 110 is moving forward while obtaining propulsion, the driving shaft 124 is elastically deformed. When the driving shaft 124 is elastically deformed in a state of not being rotated, the driving shaft 124 is deformed such that pitches on a bending-center inner side 124$i$ of the driving shaft 124 are narrowed, while pitches on a bending-center outer side 124$o$ are expanded, as shown in FIG. 1B which is an enlarged view of a part A.

Figure 1C:
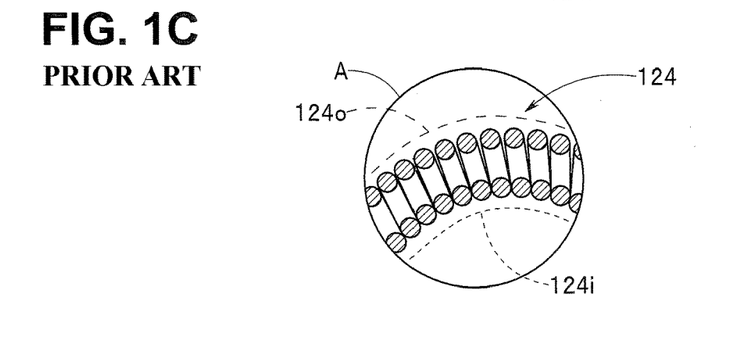
FIG. 1C is a diagram illustrating the configuration and action of the insertion portion assisting mechanism portion that the endoscope has.

In comparison, when the driving shaft 124 is elastically deformed in a state in which the driving shaft 124 transmits rotational driving force to the spiral shape portion 116 and generates propulsion for moving forward, the driving shaft 124 positioned at a bending portion is closely deformed by the pitches on the bending-center inner side 124$i$ of the driving shaft 124 being further narrowed, and the pitches on the bending-center outer side 124$o$ are narrowed and shortened without being expanded, by the force that causes the driving shaft 124 to be shortened, as shown in FIG. 1C which is an enlarged view of the part A.

SUMMARY OF THE INVENTION

An insertion apparatus of an aspect of the invention includes: a flexible tube with flexibility that is extendedly provided along a longitudinal axis; an electric driving source arranged on a proximal end side of the flexible tube and comprising an output axle configured to rotate around an axis; a driven portion arranged on a distal end side of the flexible tube and configured to be caused to move by rotational driving force of the electric driving source; and a single driving force transmitting member inserted along a longitudinal axis in the flexible tube and formed by being wound around an axis along a direction of the insertion in a coil shape, the single driving force transmitting member being configured to transmit the rotational driving force of the electric driving source to the driven portion by being rotated around the longitudinal axis by the rotational driving force of the electric driving source. For the driving force transmitting member, first torsional rigidity in a first rotating state of being rotated in a direction of being wound in the coil shape is set higher than second torsional rigidity in a second rotating state of being rotated in a direction opposite to the direction of being wound in the coil shape; and the driven portion performs a first motion by rotational driving force transmitted by the driving force transmitting member being caused to be in the first rotating state and performs a second motion requiring a larger amount of force than the first motion by rotational driving force transmitted by the driving force transmitting member being caused to be in the second rotating state.

DETAILED DESCRIPTION OF THE PREFERRED EMBODIMENT(S)

An embodiment of the present invention will be described below with reference to drawings.

Note that, on each of the drawings used in the description below, a reduced scale of each component is caused to be different so that each component is in a size recognizable on the drawing. That is, the present invention is not limited only to the number of components, shapes of the components, a ratio of sizes of the components, and relative positional relationships among the respective components shown in the drawings.

Figure 2:
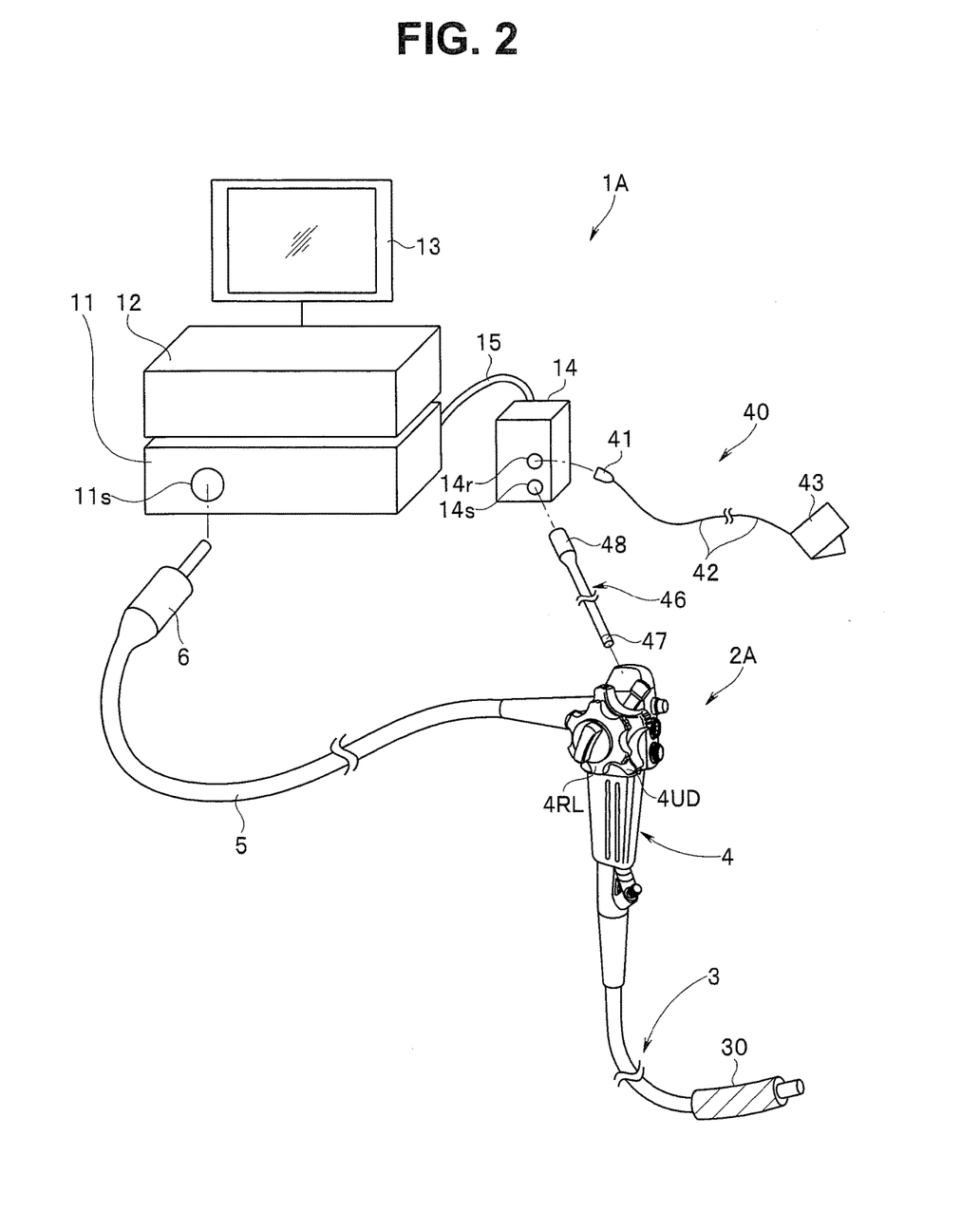
FIG. 2 is a diagram illustrating an endoscope apparatus that has the insertion assisting tool on an insertion portion of the endoscope.

As shown in FIG. 2, an insertion apparatus of the present embodiment is an endoscope apparatus 1A, and a main part is configured being provided with an endoscope 2A, a light source device 11 which is an endoscope external device, a display processor 12, a monitor 13 and a control device 14. The endoscope 2A has an insertion assisting tool 30 to be described later as an electric operation mechanism portion configured to reduce a burden on an operator. Reference numeral 15 is a connection cable, which electrically connects the light source device 11 and the control device 14.

Reference numeral 15 is a connection cable, which electrically connects the light source device 11 and the control device 14.

The light source device 11 is electrically connected to the display processor 12 via a connection cable not shown. The display processor 12 is electrically connected to the monitor 13. The control device 14 is provided with a control portion (not shown) configured to electrically perform driving control of the insertion assisting tool 30.

The endoscope 2A has an elongated insertion portion 3 to be inserted into a digestive tract of a digestive organ such as an esophagus, a stomach, a duodenum, a small intestine and a large intestine. An operation portion 4 is provided on a proximal end of the insertion portion 3, and a universal cord 5 extends from the operation portion 4. At an extended end of the universal cord 5, a connection connector 6 attachable to and detachable from a connector connecting portion 11s of the light source device 11 is provided.

Figure 3:
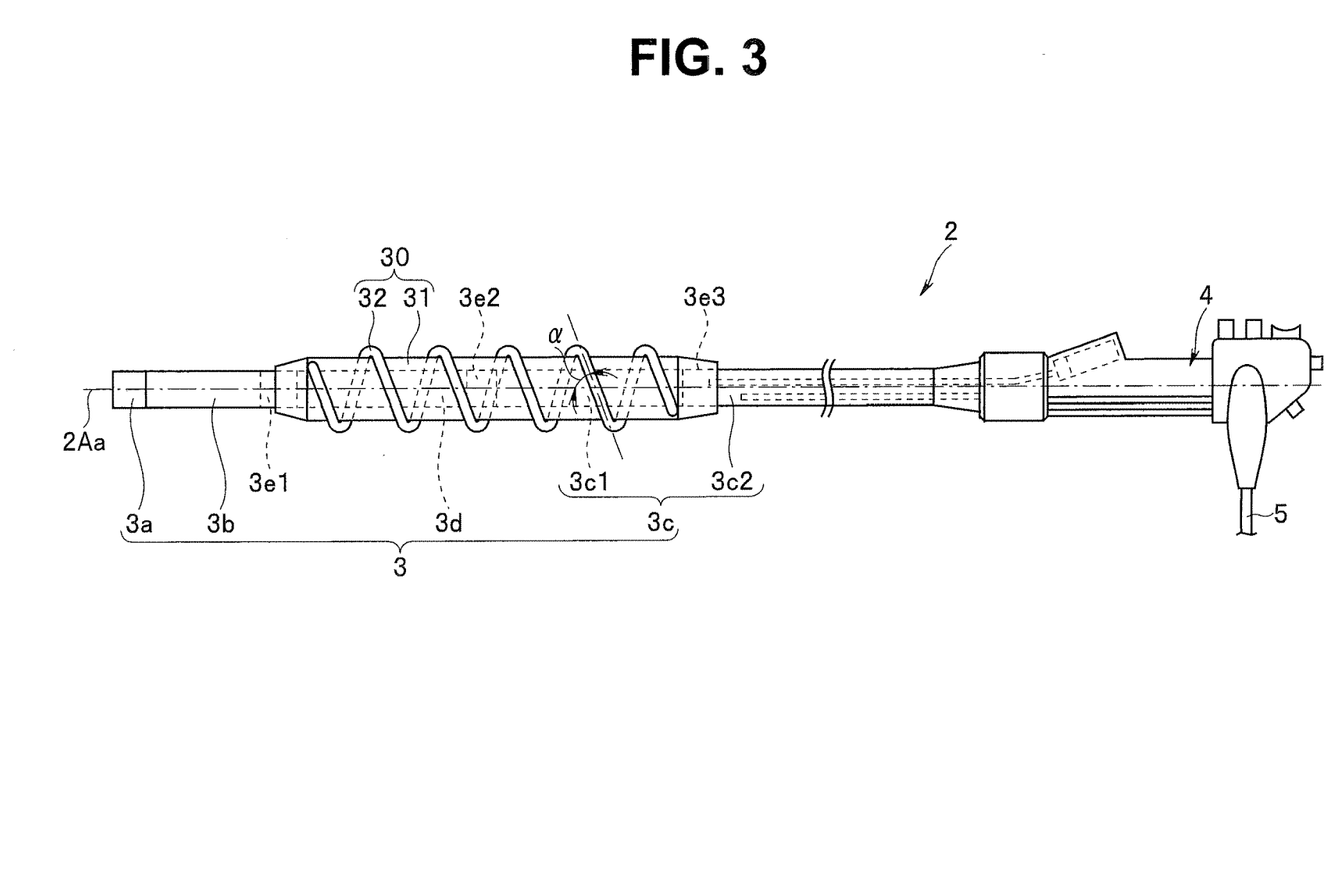
FIG. 3 is a diagram illustrating the insertion portion and the insertion assisting tool provided on a flexible tube of the insertion portion.

In the present embodiment, the endoscope 2A is, for example, an endoscope for lower digestive tract and is provided with a distal end portion 3a on a distal end side of the insertion portion 3 as shown in FIG. 3. A bending portion 3b which is bendable, for example, up and down and left and right is provided on a proximal end side of the distal end portion 3a. On a proximal end side of the bending portion 3b, a flexible tube 3c having predetermined first flexibility is provided along a longitudinal axis of the insertion portion 3.

As shown in FIG. 2, the operation portion 4 is provided with an up-down bending operation knob 4UD and a left-right bending operation knob 4RL which are bending operation devices. The operation knobs 4UD, and 4RL can freely rotate around axes of axles not shown, respectively.

The bending portion 3b is configured to perform a bending operation in a desired direction by operating the up-down bending operation knob 4UD or the left-right bending operation knob 4RL to manually pull a bending wire (not shown), similarly to a bending portion of a conventional endoscope.

As shown in FIGS. 2 and 3, the insertion assisting tool 30 is provided on a distal-end-side outer circumference of the flexible tube 3c constituting the insertion portion 3 in the present embodiment. The insertion assisting tool 30 is a driven portion and performs a first motion and a second motion by being rotated around the axis.

The second motion is a rotation motion for generating first propulsion that causes the insertion portion 3 to move forward toward a depth of a subject, and the first motion is a rotation motion for generating second propulsion that causes the insertion portion 3 to move backward from an inside of the subject to an outside.

Reference numeral 40 in FIG. 2 denotes an insertion assisting mechanism operation switch (hereinafter referred to as an external switch). The insertion assisting tool 30 is configured to rotate clockwise and counterclockwise around an axis 2Aa of the insertion portion 3 shown in FIG. 3 in response to an operation of the external switch 40.

Note that reference numeral 3d in FIG. 3 denotes a passively bending portion. The passively bending portion 3d is configured to passively bend by receiving external force. In the present embodiment, the passively bending portion 3d is arranged between the bending portion 3b and the flexible tube 3c in the insertion portion 3.

Further, in the present embodiment, the flexible tube 3c is configured with a first flexible tube 3c1 positioned on the passively bending portion 3d side, and a second flexible tube 3c2 connected to a proximal end of the first flexible tube 3c1.

The bending portion 3b and the passively bending portion 3d are connected via a first connection tube 3e1; the passively bending portion 3d and the first flexible tube 3c1 are connected via a second connection tube 3e2; and the first flexible tube 3c1 and the second flexible tube 3c2 are connected via a third connection tube 3e3.

The first connection tube 3e1 and the third connection tube 3e3 also serve as attaching portions of insertion assisting tool 30. On the first connection tube 3e1, one end portion of a tube body 31 of the insertion assisting tool 30 to be described later is arranged. On the third connection tube 3e3, the other end portion of the tube body 31 is arranged.

The insertion assisting tool 30 has the tube body 31 and a spiral shape portion 32. The spiral shape portion 32 is a projecting portion that projects from an outer circumferential surface of the tube body 31. The spiral shape portion 32 is spirally shaped, being wound clockwise toward the insertion portion distal end side which is a distal end side from the operation portion 4 side which is a proximal end side. The projecting portion projects from the outer circumferential surface of the tube body 31 toward a diameter-direction outside of the tube body 31 by a predetermined amount, and an angle α relative to the axis 2Aa is set, for example, to an angle larger than 45°.

The insertion assisting tool 30 is configured so that propulsion is generated by screw action caused by the spiral shape portion 32 coming into contact with a body cavity wall accompanying rotation caused in a winding direction around the axis or in a direction opposite to the winding direction, and the propulsion is given to the insertion portion 3.

More specifically, the insertion assisting tool 30 of the present embodiment gives the first propulsion that causes the insertion portion 3 to move forward toward a depth of a body cavity, to the insertion portion 3 by the spiral shape portion 32 being rotated clockwise, that is, in a same direction as the winding direction around the axis when the spiral shape portion 32 is seen from the operation portion 4 side (a first rotation direction).

On the other hand, by the spiral shape portion 32 being rotated counterclockwise, that is, in a direction opposite to the winding direction when the spiral shape portion 32 is seen from the operation portion 4 side (a second rotation direction), the insertion assisting mechanism portion 30 gives the second propulsion that causes the insertion portion 3 to move backward from the depth of the body cavity toward an outside of the body, to the insertion portion 3.

When the first propulsion for causing the insertion portion 3 to move forward and the second propulsion for causing the insertion portion 3 to move backward generated by the insertion assisting tool 30 are compared, the first propulsion at the time of causing the insertion portion 3 to move forward is larger than the second propulsion at the time of causing the insertion portion 3 to move backward.

This is because a load (resistance) applied to the insertion portion 3 increases as the insertion portion 3 is inserted into a body.

This is because a load (resistance) applied to the insertion portion 3 increases as the insertion portion 3 is inserted into a body. Then, the load (resistance) decreases as the insertion portion 3 is being pulled out from an inside of the body.

Figure 4:
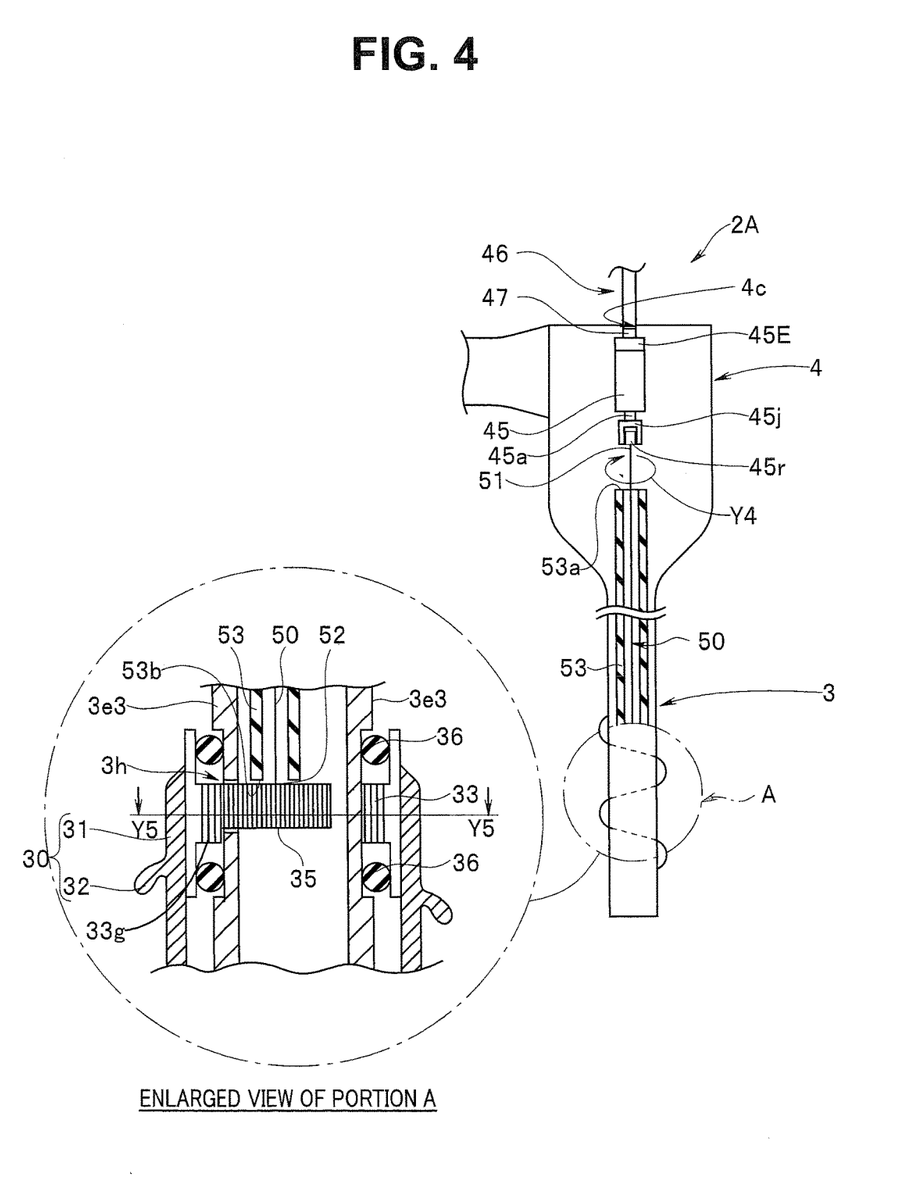
FIG. 4 is a diagram illustrating a relationship between the insertion assisting tool and an electric driving source configured to cause the insertion assisting tool to perform a rotation motion.

As shown in FIG. 4, a driving motor 45 which is an electric driving source is arranged in the operation portion 4 provided on a proximal end side of the flexible tube 3c. The driving motor 45 generates rotational driving force that causes the insertion assisting tool 30 to perform a rotation motion.

A driving axle 45a of the driving motor 45 is rotatable clockwise or counterclockwise around the axis when seen from a motor proximal end side as shown by an arrow Y4. Clockwise rotational driving force or counterclockwise rotational driving force is transmitted to the insertion assisting tool 30 by a driving shaft 50 which is a rotational driving force transmitting member.

The driving shaft 50 is insertedly disposed along a longitudinal axis in the flexible tube 3c of the endoscope 2A in a state of being covered with a soft protection tube 53. A first end portion 51 of the driving shaft 50 projects from a first side end 53a of the protection tube 53, and a second end portion 52 projects from a second end side end 53b of the protection tube 53.

The driving shaft 50 of the present embodiment is a flexible shaft having predetermined second flexibility and is provided with flexibility higher than the first flexibility of the flexible tube 3c in a natural state of not being rotated. The flexible shaft is formed by winding special hard steel wires or stainless steel wires for spring clockwise and counterclockwise alternately to form several layers.

In the present embodiment, for example, a main winding direction of the driving shaft 50 is set counterclockwise by causing a winding direction of an outermost layer wire to be counterclockwise. That is, the driving shaft 50 is a shaft for left rotation for which torsional rigidity for left rotation is set higher than torsional rigidity for right rotation in advance.

Note that the main winding direction of the driving shaft 50 may be set counterclockwise by causing the winding direction of not the outermost layer wire but an intermediate layer wire to be counterclockwise.

The first end portion 51, which is an end portion of the driving shaft 50 disposed in the operation portion 4, is coupled with the driving axle 45a of the motor 45. More specifically, a coupling portion 45j is integrally and fixedly provided on the driving axle 45a of the motor 45. The first end portion 51 of the driving shaft 50 is integrally and fixedly provided on a coupling rod 45r. The coupling rod 45r can freely move forward and backward in a longitudinal axis direction relative to the coupling portion 45j and is engagedly disposed capable of transmitting rotation force.

In the present embodiment, the insertion assisting tool 30 rotates in the first rotation direction or the second rotation direction when seen from a proximal end side of the operation portion 4, accompanying a switch operation of the external switch 40.

As shown in FIG. 2, the external switch 40 is configured being provided with a foot switch connecting portion 41, a foot switch cable 42 and a foot switch portion 43.

The foot switch connecting portion 41 is attachable to and detachable from a foot switch connection port 14r of the control device 14. The foot switch portion 43 is provided with a switching switch (not shown). By operating the switching switch, switching to rotation in the first rotation direction, rotation in the second rotation direction or a stop state can be performed.

Further, the foot switch portion 43 may be configured so that rotation speed of the motor 45 changes according to magnitude of an amount of depression.

Reference numeral 46 denotes an electric cable. The electric cable 46 is provided with a first connecting portion 47 and a second connecting portion 48. The first connecting portion 47 is attachable to and detachable from an electric connecting portion (reference numeral 4c in FIG. 4) provided on the operation portion 4. In comparison, the second connecting portion 48 is attachable to and detachable from a cable connection port 14s of the control device 14.

By a depressing operation of the switching switch of the foot switch portion 43 being performed and an instruction signal being outputted to the control portion of the control device 14 in a state in which the first connecting portion 47 of the electric cable 46 is connected to the electric connecting portion 4c and the second connecting portion 48 is connected to the cable connection port 14s, a motor driving signal is generated. The generated motor driving signal is outputted to the motor 45 via the electric cable 46.

As a result, the driving axle 45a of the motor 45 is switched to a state of rotating clockwise relative to the axis or a state of rotating counterclockwise relative to the axis, or switched from a rotating state to a stop state.

Note that the motor 45 enters the stop state, for example, when the switching switch of the foot switch portion 43 is in an undepressed state.

Further, a signal line connected to a motor encoder 45E is inserted in the electric cable 46. A rotation direction and rotation speed of the motor 45 are detected by the motor encoder 45E and, after that, outputted to the control portion of the control device 14 via the signal line in the electric cable 46.

According to the configuration, the driving shaft 50 is rotated, accompanying clockwise or counterclockwise rotation of the driving axle 45a of the motor 45. That is, by the driving axle 45a of the motor 45 being rotationally driven clockwise relative to the axis, the driving shaft 50 rotates in the same direction; and, by the driving axle 45a being rotationally driven counterclockwise relative to the axis, the driving shaft 50 rotates in the same direction.

Figure 5:
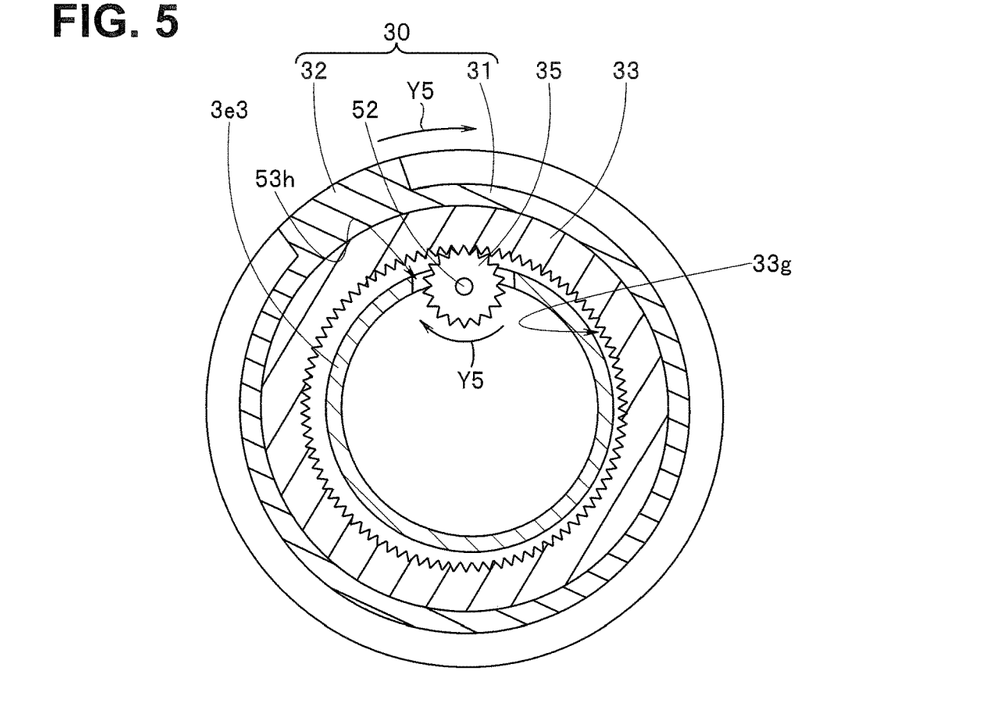
FIG. 5 is a cross-sectional diagram along a Y5-Y5 line in FIG. 4.

On the other hand, the second end portion 52, which is an end portion of the driving shaft 50 and disposed in the flexible tube 3c, is integrally fixed to a transmission gear 35. As shown in FIGS. 4 and 5, the transmission gear 35 is meshed with a gear portion 33g formed on an internal circumferential surface of an annular tube body rotating portion 33. According to the configuration, accompanying rotation of the driving shaft 50, the transmission gear 35 is rotated in the same direction; and, accompanying rotation of the transmission gear 35, the tube body rotating portion 33 is rotated in the same direction.

An outer circumferential surface of the tube body rotating portion 33 is integrally and fixedly provided on the tube body 31 of the insertion assisting tool 30. The gear portion 33g is disposed, projecting outward from an outer circumferential surface of the third connection tube 3e3, passing through a through hole 3h communicating with an inside and an outside, which is provided in the third connection tube 3e3.

A width of the through hole 3*h* is set to a dimension predetermined in consideration of a thickness dimension of the transmission gear 35 in order to restrict movement of the transmission gear 35 in an axial direction.

Reference numeral 36 denotes an O-shaped ring. A pair of O-shaped rings 36 are disposed not only in close contact with the internal circumferential surface of the tube body rotating portion 33 but also in close contact with the outer circumferential surface of the third connection tube 3*e*3. The tube body rotating portion 33 is integrated with the tube body 31 of the insertion assisting tool 30 which is freely rotatable relative to the insertion portion 3.

As a result, watertightness between the internal circumferential surface of the tube body rotating portion 33 and the outer circumferential surface of the third connection tube 3*e*3 is maintained.

In the present embodiment, at time of obtaining the first propulsion that causes the insertion portion 3 to move forward, the driving axle 45*a* of the motor 45 is rotated as shown by the arrow Y4 in FIG. 4. Then, the driving shaft 50 rotates in a direction opposite to the winding direction for which torsional rigidity is set higher.

By the driving shaft 50 being rotated in the direction of the arrow Y4, the transmission gear 35 is also rotated in a direction of an arrow Y5 in FIG. 5 as shown in FIG. 5, and the tube body rotating portion 33 is also rotated in the direction of the arrow Y5. As a result, the insertion assisting tool 30 is rotated in the first rotation direction and enters a rotating state in which the first propulsion is generated.

As a result, it becomes possible for the operator to, while obtaining the first propulsion that causes the insertion portion 3 to move forward from the insertion assisting tool 30, insert the insertion portion 3 to a depth.

Note that the driving shaft 50 is not limited to a flexible shaft but may be a torque coil, a torque wire or the like which is a multi-threaded and multi-layered coil if torsional rigidity when the driving shaft 50 is rotated in the winding direction is different from torsional rigidity when the driving shaft 50 is rotated in the direction opposite to the winding direction.

Action of the endoscope apparatus 1A will be described.

In the endoscope apparatus 1A, the connection connector 6 of the endoscope 2A is connected to the connector connecting portion 11*s*. The first connecting portion 47 of the electric cable 46 is connected to the electric connecting portion 4*c* of the operation portion 4, and the second connecting portion 48 is connected to the device connection port 14*s* of the control device 14. The foot switch connecting portion 41 of the external switch 40 is connected to the foot switch connection port 14*r* of the control device 14.

The operator can obtain a state in which the first propulsion is generated or a state in which the second propulsion is generated, by appropriately performing an operation of depressing the switching switch provided on the foot switch portion 43 of the external switch 40.

At time of operating the endoscope 2A of the endoscope apparatus 1A, the operator causes the light source device 11, the display processor 12, the monitor 13 and the control device 14 to be in a driven state. After that, while observing an endoscopic image displayed on the monitor 13, the operator performs a hand-side operation to insert the insertion portion 3, for example, from an anus toward a small intestine.

At this time, the operator operates the switching switch of the foot switch portion 43 as necessary to cause the insertion portion 3 to move forward while obtaining the first propulsion. That is, the operator causes the driving axle 45*a* of the motor 45 to rotate as shown by the arrow Y4 in FIG. 4 to rotate the driving shaft 50 in the direction opposite to the winding direction for which torsional rigidity is set higher.

Accompanying the rotation of the driving shaft 50, the transmission gear 35 and the tube body rotating portion 33 are also rotated in the same direction. As a result, the insertion assisting tool 30 is rotated in the first rotation direction, which is the winding direction, and it becomes possible to perform insertion to a depth while obtaining the first propulsion.

In the present embodiment, when the flexible tube 3*c* of the insertion portion 3 of the endoscope 2A passes, for example, through a bent portion of a sigmoid colon or the like, the driving shaft 50 disposed in the second flexible tube 3*c*2 is elastically deformed.

Figure 6A:
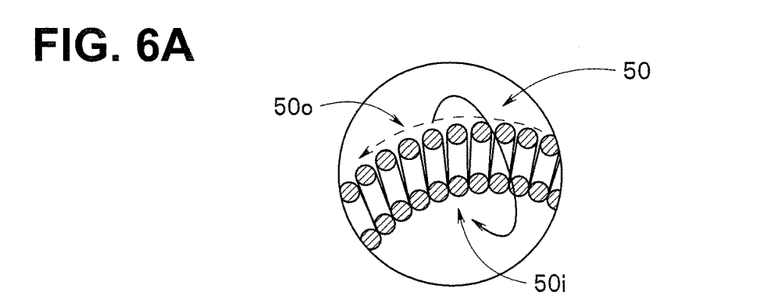
FIG. 6A is a diagram illustrating action of a rotational driving force transmitting member.

At the time, since the direction in which the driving shaft 50 rotates is the direction opposite to the winding direction, the driving shaft 50 is not shortened even in a state in which driving force is being transmitted, and the deformed state is maintained without pitches on a bending-center inner side 50*i* of the driving shaft 50 positioned at the bent portion being further narrowed as shown in FIG. 6A. On the other hand, pitches on a bending-center outer side 50*o* are not narrowed, in other words, not shortened since the driving shaft 50 is slightly deformed in a direction in which the driving shaft 50 is lengthened, and the deformed state is maintained.

Therefore, in the present embodiment, the driving shaft 50 is held in a state of being engagedly disposed, in a driving force transmitting state in which the first propulsion is obtained, without the coupling rod 45*r* falling off from the coupling portion 45*j*.

Further, since the driving shaft 50 is not shortened in the driving force transmitting state in which the first propulsion is obtained, the second flexibility is maintained. Therefore, it is prevented that flexibility of the driving shaft 50 decreases and, thereby, flexibility of the flexible tube 3*c* decreases lower than the first flexibility.

As a result, it becomes possible for the operator to give the first propulsion from the insertion assisting tool 30 to the insertion portion 3 which is in the state in which the flexible tube 3*c* maintains the first flexibility, cause the distal end portion 3*a* of the insertion portion 3 to pass through a large intestine, and smoothly insert the distal end portion 3*a* toward a small intestine.

Note that, when judging from an endoscopic image that the distal end portion 3*a* has reached a target region, the operator releases the operation of depressing the foot switch portion 43 and stops rotation of the insertion assisting tool 30.

Next, the operator performs endoscopy while performing an operation of pulling back the insertion portion 3. At the time, the operator selects whether to cause the insertion portion 3 to move backward by a hand-side operation or to cause the insertion portion 3 to move backward while obtaining the second propulsion.

In the case of performing endoscopy while pulling back the insertion portion 3 by a hand-side operation, the operator causes rotation of the insertion assisting tool 30 to enter the stop state and pulls out the insertion portion 3. On the other hand, in the case of performing endoscopy by pulling out the insertion portion 3 while obtaining the second propulsion, the operator operates the switching switch of the foot switch portion 43 to select the second propulsion.

As a result, the driving axle 45*a* of the motor 45 reversely rotates relative to the arrow Y4 in FIG. 4, that is, rotates in a direction opposite to the direction described before, and causes the driving shaft 50 to rotate in the winding direction for which torsional rigidity is set higher.

Accompanying the rotation of the driving shaft 50, the transmission gear 35 and the tube body rotating portion 33 are also rotated in the same direction. As a result, the insertion assisting tool 30 is rotated in the second rotation direction, which is the direction opposite to the winding direction, and it becomes possible to perform insertion to a depth while obtaining the second propulsion.

The second propulsion required at the time of pulling out the insertion portion 3 is smaller in comparison with the first propulsion described before. Therefore, rotational driving force transmitted from the motor 45 to the driving shaft 50 at the time of pulling out the insertion portion 3 is set smaller than rotational driving force transmitted from the motor 45 to the driving shaft 50 at the time causing the insertion portion 3 to move forward, in advance.

Figure 6B:
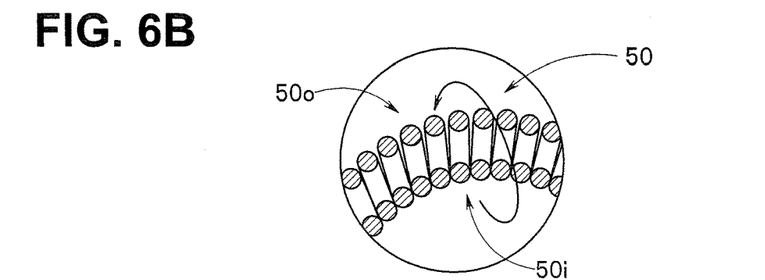
FIG. 6B is a diagram illustrating action of the rotational driving force transmitting member.

Therefore, when the driving shaft 50 is positioned at the bent portion, the driving shaft 50 is maintained in a deformed state without the pitches on the bending-center inner side 50i of the driving shaft 50 being narrowed as shown in FIG. 6B, though the driving shaft 50 is rotated in the winding direction. Further, the driving shaft 50 is maintained in the deformed state without the pitches on the bending-center outer side 50o being shortened.

Therefore, in a driving force transmitting state in which the second propulsion is obtained, the driving shaft 50 is prevented from being shortened, and the coupling rod 45r is prevented from falling off from the coupling portion 45j. Further, since it does not happen that the second flexibility is decreased by the driving shaft 50 being shortened, it is prevented that the flexibility of the driving shaft 50 decreases and, thereby, the flexibility of the flexible tube 3c decreases lower than the first flexibility.

As a result, it becomes possible for the operator to give the second propulsion from the insertion assisting tool 30 to the insertion portion 3 which is in the state in which the flexible tube 3c maintains the first flexibility, cause the distal end portion 3a of the insertion portion 3 to pass through a large intestine, and smoothly pull out the distal end portion 3a.

As described above, in the endoscope 2A provided with the insertion assisting tool 30 configured to give the first propulsion or the second propulsion, which is smaller in comparison with the first propulsion to the insertion portion 3, on the distal end side of the flexible tube 3c, when the insertion assisting tool 30 is caused to rotate in the first rotation direction, which is the winding direction, to generate the first propulsion, the driving shaft 50 is caused to rotate by the motor 45 in the direction opposite to the winding direction for which torsional rigidity is higher to transmit predetermined rotational driving force set in advance to the insertion assisting tool 30.

On the other hand, when the insertion assisting tool 30 is caused to rotate in the second rotation direction to generate the second propulsion, the driving shaft 50 is caused to rotate in the winding direction for which torsional rigidity is higher by the motor 45, and rotational driving force that is smaller in comparison with the rotational driving force that generates the first propulsion is transmitted to the insertion assisting tool 30.

As a result, the trouble is resolved that, at the time of transmitting the rotational driving force of the motor 45 to the insertion assisting tool 30 via the driving shaft 50, the driving shaft 50 is shortened, and the coupling rod 45r falls off from the coupling portion 45j, and it is possible to prevent the operation portion 4 from being upsized.

Further, a trouble is resolved that, by the flexibility of the driving shaft 50 being decreased by the driving shaft 50 being shortened, the flexibility of the flexible tube 3c decreases lower than the first flexibility, and it becomes difficult for the insertion portion 3 to move forward and backward by propulsion.

Note that, in a configuration in which the coupling rod 45r is provided on the second end portion 52, and the coupling portion 45j is provided on the transmission gear 35, the first end portion 51 is integrally and fixedly provided on the driving axle 45a.

According to the configuration, it is possible to certainly prevent the trouble that the coupling rod 45r falls off from the coupling portion 45j by the driving shaft 50 being shortened, and it is possible to resolve a trouble that a rigid length of the flexible tube 3c constituting the insertion portion 3 is increased.

Further, the spiral shape portion 32 may be formed so that the winding direction is a counterclockwise direction opposite to the direction described above. In the configuration, the driving shaft is shaft for right rotation, and torsional rigidity for right rotation is set higher than torsional rigidity for left rotation. By causing the driving shaft to rotate in the direction opposite to the winding direction and causing the spiral shape portion 32 to rotate in the winding direction similarly to the above description, action and effects similar to the action and effects described before can be obtained.

Furthermore, though the motor 45 is arranged in the operation portion 4 in the embodiment described above, the motor 45 may be provided in the connection connector 6 provided at the extended end of the universal cord 5.

In the configuration, it is possible to resolve a trouble that flexibility of the universal cord 5 is decreased by the driving shaft 50 being shortened, in addition to the action and effects described above.

In a case of causing the driving shaft 50 to be insertedly disposed in the universal cord 5 to drive the driven members provided in the operation portion, for example, an electric bending mechanism and a power assist mechanism configured to drive a pulling mechanism for bending wires, it is also possible to resolve the trouble that the coupling rod 45r falls off from the coupling portion 45j by the driving shaft 50 being shortened, and it is possible to prevent the operation portion from being upsized and resolve the trouble that the flexibility of the universal cord 5 decreases.

In a general endoscope, an amount of force required for a motion of causing a bending portion to bend from a neutral position in an upward direction on an observation screen is larger than an amount of force required for a motion of bending the bending portion in other directions. Therefore, it is recommended to, in an endoscope provided with an electric bending mechanism, use a rotation direction in which the driving shaft 50 is shortened for an upward bending motion of the bending portion.

Note that the present invention is not limited to the embodiment described above, but various modifications can be practiced within a range not departing from the spirit of the invention. For example, rigidity may be caused to be higher for a rotation direction of a torque shaft that causes a bending portion to bend in a right direction when the torque shaft is rotated.

Note that the present invention is not limited to the embodiment described above, but various modifications can be practiced within the range not departing from the spirit of the invention. For example, the insertion apparatus is not limited to an endoscope but may be a treatment instrument used inside which is configured to be inserted into a treatment instrument channel of an endoscope, a guide tube configured to guide an endoscope into a body, or the like.

According to the present invention, it is possible to realize an insertion apparatus capable of resolving a problem that the end portion of the driving shaft falls off from a coupling portion by a driving shaft being shortened and a problem that flexibility of a flexible tube decreases that are caused at time of inserting an insertion portion into a digestive tract of a digestive organ, and obtaining rotational driving force transmitted by the driving shaft to reduce a burden on an operator.

What is claimed is:

1. An insertion apparatus comprising:
a flexible tube with flexibility that is extendedly provided along a longitudinal axis;
an electric driving source arranged on a proximal end side of the flexible tube and comprising an output axle configured to rotate around an axis;
a driven portion arranged on a distal end side of the flexible tube and configured to be caused to move by rotational driving force of the electric driving source; and
a single driving force transmitting member inserted along a longitudinal axis in the flexible tube and formed by being wound around an axis along a direction of the insertion in a coil shape, the single driving force transmitting member being configured to transmit the rotational driving force to the driven portion by being rotated around the longitudinal axis by the rotational driving force; wherein
the driving force transmitting member has torsional rigidity in a winding direction of the coil that is higher than in an opposite direction of the winding direction; and
the driven portion is configured to perform a first motion by rotational driving force transmitted by the driving force transmitting member being caused to be in a first rotating state in which the driving force transmitting member rotates in the winding direction and to perform a second motion requiring a larger amount of force than the first motion by rotational driving force transmitted by the driving force transmitting member being caused to be in a second rotating state in which the driving force transmitting member rotates in the opposite direction of the winding direction.

2. The insertion apparatus according to claim 1, wherein the driven portion is an insertion assisting tool comprising a tube body and a spiral shape portion formed in a spiral shape by winding a projecting portion projecting from an outer circumferential surface of the tube body from a proximal end side to a distal end side in a predetermined direction; and
the insertion assisting tool performs the second motion of generating second propulsion that causes an insertion portion to move forward toward a depth of a digestive tract of a digestive organ, by the rotational driving force transmitted by the driving force transmitting member being caused to be in the second rotating state.

3. The insertion apparatus according to claim 2, wherein the driving force transmitting member has flexibility higher than the flexible tube; and
the rotational driving force transmitted to the insertion assisting tool by the driving force transmitting member being caused to be in the first rotating state is set in advance smaller than the rotational driving force transmitted to the insertion assisting tool by the driving force transmitting member being caused to be in the second rotating state.

4. An insertion apparatus comprising:
a flexible tube with flexibility that is extendedly provided along a longitudinal axis;
an electric driving source arranged on a proximal end side of the flexible tube and comprising an output axle configured to rotate around an axis;
a driven portion arranged on a distal end side of the flexible tube and configured to be caused to move by rotational driving force of the electric driving source;
a single driving force transmitting member inserted along a longitudinal axis in the flexible tube and formed by being wound around an axis along a direction of the insertion in a coil shape, the single driving force transmitting member being configured to transmit the rotational driving force to the driven portion by being rotated around the longitudinal axis by the rotational driving force; and
a coupling rod coupled with an end portion of the driving force transmitting member, the coupling rod being engagedly disposed in a coupling portion coupled with the electric driving source, so as to be movable forward and backward in a longitudinal axis direction and to transmit a rotational driving force, wherein
the driving force transmitting member has torsional rigidity in a winding direction of the coil that is higher than in an opposite direction of the winding direction, the driving force transmitting member being configured to shorten according to torsion in the winding direction; and
the driven portion is configured to perform a first motion by rotational driving force transmitted by the driving force transmitting member being caused to be in a first rotating state in which the driving force transmitting member rotates in the winding direction and to perform a second motion requiring a larger amount of force than the first motion by rotational diving force transmitted by the driving force transmitting member being caused to be in a second rotating state in which the driving force transmitting member rotates in the opposite direction of the winding direction.

* * * * *